United States Patent [19]

Demisch et al.

[11] Patent Number: 5,733,436

[45] Date of Patent: Mar. 31, 1998

[54] METHOD FOR DETERMINING THE STATE OF AN ELECTROCHEMICAL GAS SENSOR

[75] Inventors: Ullrich Demisch, Freiburg; Joerg Pahlke, Titisee-Neustadt; Peter Ziegler, Lenzkirch, all of Germany

[73] Assignee: Testo GmbH & Co., Lenzkirch, Germany

[21] Appl. No.: 618,491

[22] Filed: Mar. 19, 1996

[30] Foreign Application Priority Data

Mar. 23, 1995 [DE] Germany .................. 195 10 574.5

[51] Int. Cl.6 .................................................. G01N 27/26
[52] U.S. Cl. .................. 205/775; 204/401; 204/431; 205/785.5
[58] Field of Search ...................... 204/401, 415, 204/431; 205/775, 780.5, 781, 782, 782.5, 783, 786.5

[56] References Cited

U.S. PATENT DOCUMENTS

| 4,735,691 | 4/1988 | Green et al. | 204/415 |
| 4,921,582 | 5/1990 | Wang et al. | 204/415 |
| 5,273,640 | 12/1993 | Kusanagi et al. | 204/415 |
| 5,405,512 | 4/1995 | Parker | 204/401 |

Primary Examiner—T. Tung
Attorney, Agent, or Firm—R. Lewis Gable

[57] ABSTRACT

This invention relates to a process for determining the state of an electrochemical gas sensor located in an environment with a known and constant concentration of a gas which is to be detected, where said gas to be detected is converted by chemical reaction at a three-phase boundary formed by a measuring electrode, an electrolyte and the gas to be detected, and where a current flowing in an external circuit functions as a sensor signal, whereby for determination of the state of the gas sensor, the external circuit is temporarily interrupted, and during this time the gas sensor is in specific exposure with the gas to be detected, and the resulting transient of the sensor is recorded and evaluated over time after the external circuit is closed.

9 Claims, 2 Drawing Sheets

METHOD FOR DETERMINING THE STATE OF AN ELECTROCHEMICAL GAS SENSOR

FIELD OF THE INVENTION

The invention relates to a method for the determination of the state of an electrochemical gas sensor located in an environment with a known and constant concentration of a gas which is to be detected, where said gas to be detected is converted by chemical reaction at a three-phase boundary formed by a measuring electrode, an electrolyte and the gas to be detected, and where a current flowing in an external circuit functions as a sensor signal.

BACKGROUND OF THE INVENTION

Electrochemical gas sensors are known. They are amperometrically operating, diffusion-controlled, galvanic fuel cells in which the test gas is converted at the three-phase boundary of gas/measuring electrode/electrolyte by way of a chemical reaction. The electric current which is being conducted into an external circuit functions here as a sensor signal.

The reactant required for the compensation reaction can be a gas and may also diffuse into the sensor, which is the case, for example, with $O_2$ for the CO sensor, or it may function as a counterelectrode already stored in the sensor, such as, for example, Pb for the $O_2$ sensor.

In the latter case, the life of the sensor is significantly limited by the fact that with an increasing consumption of the counterelectrode or as a result of increasing build-up of reaction products on the counterelectrode, the compensation reaction can no longer take place. The resulting rapid drop in sensitivity occurs within a fraction of the total useful life.

With increasing age, the sensitivity of the sensor is indeed somewhat reduced by various degradation processes inside the sensor; it is, however, not possible to safely predict the time of the rapid drop of the sensor signal at the end of its life by observing and checking the sensitivity alone.

In order to be able to recognize the age-related failure of a sensor in a timely manner, suitable criteria providing the respective information and an indication of the current stage of consumption of the sensor are required.

German Patent DE 34 18 034 C2, for example, describes a method for testing a membrane-covered, polarographic sensor in which, in order to check the electrolyte change, the potential difference between the measuring electrode and the counterelectrode is monitored by using an additional electrode and by using this value for assessing the sensor function.

According to the state of the art, the current sensor sensitivity in electrochemical gas sensors is therefore compared to that sensitivity existing a short time after the sensor was manufactured. If the sensitivity loss has become too high, the sensor is replaced. Although this method offers some assurance that the used sensors are always functional, the rather pragmatically planned sensor replacement results in significant expenditures since, for safety reasons, the replacement will be made too early rather than upon reaching an unacceptable aging state.

WIPO Patent Document WO 92/21962 describes a process for monitoring the functionality of pH probes in which rectangular pulses with variable amplitude and length are supplied to a measuring probe immersed in the measuring medium, and the voltage which was modified by the probe impedance is measured and compared with the set value for an intact probe.

A similar method used for the continuous monitoring of an electrode system for potentiometric measurements is known from European Patent Publication No. 04 19 769 A2. The monitoring is performed with symmetrical bipolar current pulses which are acting on the electrodes. The resulting voltage variation is also compared to a calculated and experimentally determined set value. Other potentiometric gas sensors are known from U.S. Pat. No. 4,189,367 A1 and European Patent Publication No. 02 41 601 A1.

Based on this state of the art, it is therefore an objective of this invention to create a method of the initially mentioned type which can be used to determine the time for a replacement of a gas sensor on the basis of its age as accurately as possible in order to provide the longest possible safe useful life of the gas sensor, and which is characterized by simple handling in the sense of user-friendly performance.

SUMMARY OF THE INVENTION

According to the invention, it is provided, for the determination of the state of the gas sensor, that an external circuit is temporarily interrupted or opened, that during this time the gas sensor is in specific exposure with the gas to be detected, and that the behavior of the sensor signal is recorded and evaluated over time after the external circuit is closed.

The starting point of the process according to the invention is the idea that even during an interruption of the circuit the electrochemical conversion is temporarily maintained, with electrons and ions being produced. Since the electrons are unable to flow off, they polarize the gas sensor's electrodes. The chemical process stops when the polarization of the electrodes prevents any further ion flow in the electrolyte. The time at which this point is reached depends on the remaining activity of the measuring electrode and the number of places at the counterelectrode available for the compensation reaction, as well as the state of the electrolyte, i.e., it depends on the overall activity reserves of the gas sensor.

In a microscopic model, when polarization is complete, all catalysis centers at the surface(s) of the electrodes are covered with gas molecules which, in a sense, are waiting to dissolve and contribute to the current flow in this state, the gas sensor inside is saturated from the diffusion barrier to the measuring electrode with the gas to be detected, while during normal, diffusion-limited operation the gas concentration at the measuring electrode moves towards zero.

According to an advantageous further embodiment of the method according to the invention, it can also be provided that the gas sensor is exposed with the gas to be detected in a constant concentration while the external circuit is interrupted.

Another preferred embodiment of the method according to the invention provides that the peak value of the signal following reconnection is used as a basis for assessing the current state of the electrochemical gas sensor.

According to further embodiments of the invention, the steepness in the signal drop shortly after reconnection and/or the time for stabilizing the signal can be used additionally or alternatively as a basis for assessing the current state of the electrochemical gas sensor. This means that in certain cases all criteria mentioned are used together or, alternatively, by themselves alone.

According to a further embodiment of the invention, the method is suitable for monitoring all electrochemical gas sensors, independently of whether the tested sensors are oxygen sensors with or without an internal load resistor, or whether they are sensors for dissolved oxygen or sensors for toxic gases.

DESCRIPTION OF THE DRAWINGS

The invention, advantageous embodiments of the invention, and special advantages of the invention are explained in detail and described in reference to an exemplary embodiment in the drawings, in which.

DESCRIPTION OF A PREFERRED EMBODIMENT OF THE INVENTION

The following explanations refer to an electrochemical gas sensor which is exposed to a gas to be detected. If the sensor is in an environment containing the gas to be detected in a constant and known concentration, an external circuit is interrupted or disconnected for a specific time and is then closed again or reconnected. The behavior of the sensor signal is observed over time following the reconnection and is evaluated.

Even during an interruption of the circuit, the electrochemical conversion is temporarily maintained, while the production of electrons and ions is continued. Since the electrons are unable to flow off, they polarize the electrodes. The chemical process stops when the polarization of the electrodes prevents any further ion flow in the electrolyte. The time at which this point is reached depends on the remaining activity of the measuring electrode and the number of places at the counterelectrode available for the compensation reaction, as well as the state of the electrolyte, i.e., it depends on the overall activity reserves of the sensor.

In a microscopic model, when polarization is complete all catalysis centers at the surface(s) of the electrodes are covered with gas molecules which, in a sense, are waiting to dissolve and contribute to the current flow. In this state, the sensor inside is saturated by a diffusion barrier formed on the measuring electrode by the molecules of the gas to be detected. During normal, diffusion-limited operation, the gas concentration at the measuring electrode is reduced to zero.

Figure 1:
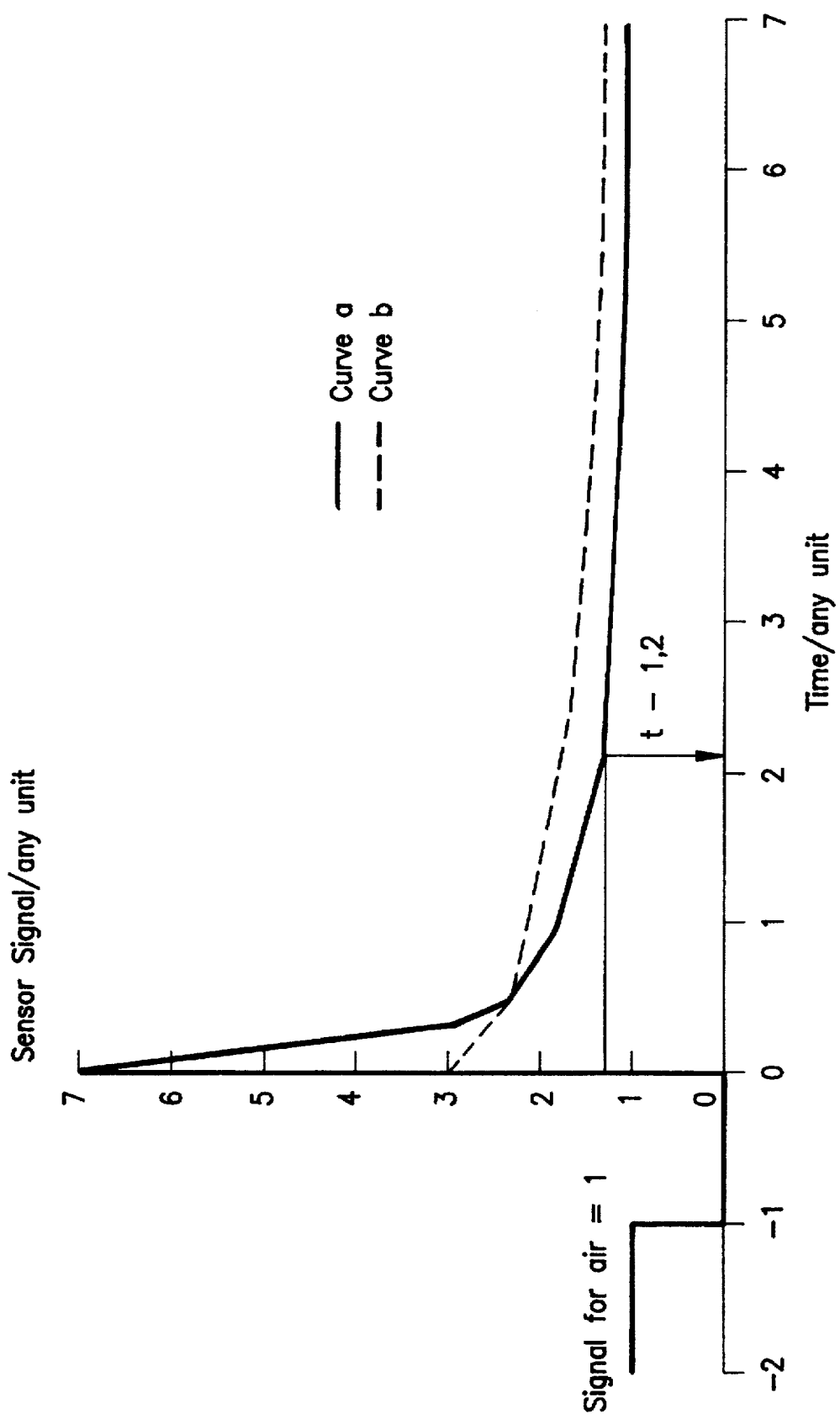
FIG. 1 shows the relationship between the degree of aging and the stabilization time for the tested sensors.

Following reconnection, a high signal and then a signal stabilization are measured in the initial state. This behavior is illustrated in FIG. 1. Depending on the type and state of consumption of the sensor, this transient signal may differ.

In many types of sensors, such as the carbon monoxide sensor, the compensation reaction takes place using oxygen from air which has been diffused in. The reaction product is a gas which escapes from the sensor. In the case of the example of a carbon monoxide sensor, the reaction product is carbon dioxide. The state of the electrodes is decisive here. From a microscopic standpoint, the signal amplitude after reconnection correlates with the number of still active catalysis centers; the number of the latter will again decrease with an increasing sensor age because of various degradation effects.

The time necessary for signal stabilization is a measure of the speed with which the gas molecules that have accumulated on the measuring electrode inside the sensor can be removed until the diffusion-limited operating snare has been reestablished. The degradation takes place by way of diffusion of a gas molecule to a free catalysis center and its subsequent electrochemical conversion. The number of catalysis centers decreases with increasing degradation, so that this process is slowed, and the time for signal stabilization simultaneously increases.

In sensors such as a two-electrode oxygen sensor in which lead is stored as a reactant in the sensor and the reaction product lead oxide remains in the sensor, the degree of coverage of the counterelectrodes with reaction products is decisive, as was described above. The number of spaces at which the opposing reaction is able to take place decreases with an increasing degree of coverage, until this becomes the limiting factor of the entire process.

The more the aging of a sensor has progressed, the smaller the signal peak on reconnection, and the longer the time necessary for stabilization. This is illustrated in FIG. 1, whereby Curve A describes the behavior of an unspent sensor, and Curve B describes the behavior of a spent sensor. This means that the amplitude of the signal peak and the stabilization time can be used as criteria for a diagnosis of the state of the sensor.

A further criterion, which can possibly be used for assessment, is the steepness of the drop of the signal shortly after reconnection.

The described method was used to test oxygen sensors with environmental air having a constant oxygen concentration. The respective, stable signal for air at the test time and shortly after manufacture of these sensors, i.e., the sensitivity loss over the past life, was known. In the tested sensors, the loss ranged from 7% to 50%, concentrating at approximately 20%.

FIG. 1 shows the transients for sensors spent to a varying degree. The transient in each case is composed of the peak level occurring shortly before power-up and before the subsequent drop of the sensor signal which is being evaluated over time.

With increasing interruption time, a saturation is observed for the signal peak and the stabilization time. A standard interruption time of 60 seconds was selected.

Given an interruption of 60 seconds, the signal peak, after reconnection, varied between 1.64 and 6.67 mA; this was 5.5 to 18.6 times the value of the respective signal in air. The stabilization time selected was the time necessary for a drop to 1.2 times the stable signal in air ("t−1.2", see also FIG. 1). Here the measured values range from 14 to 46 seconds.

Figure 2:
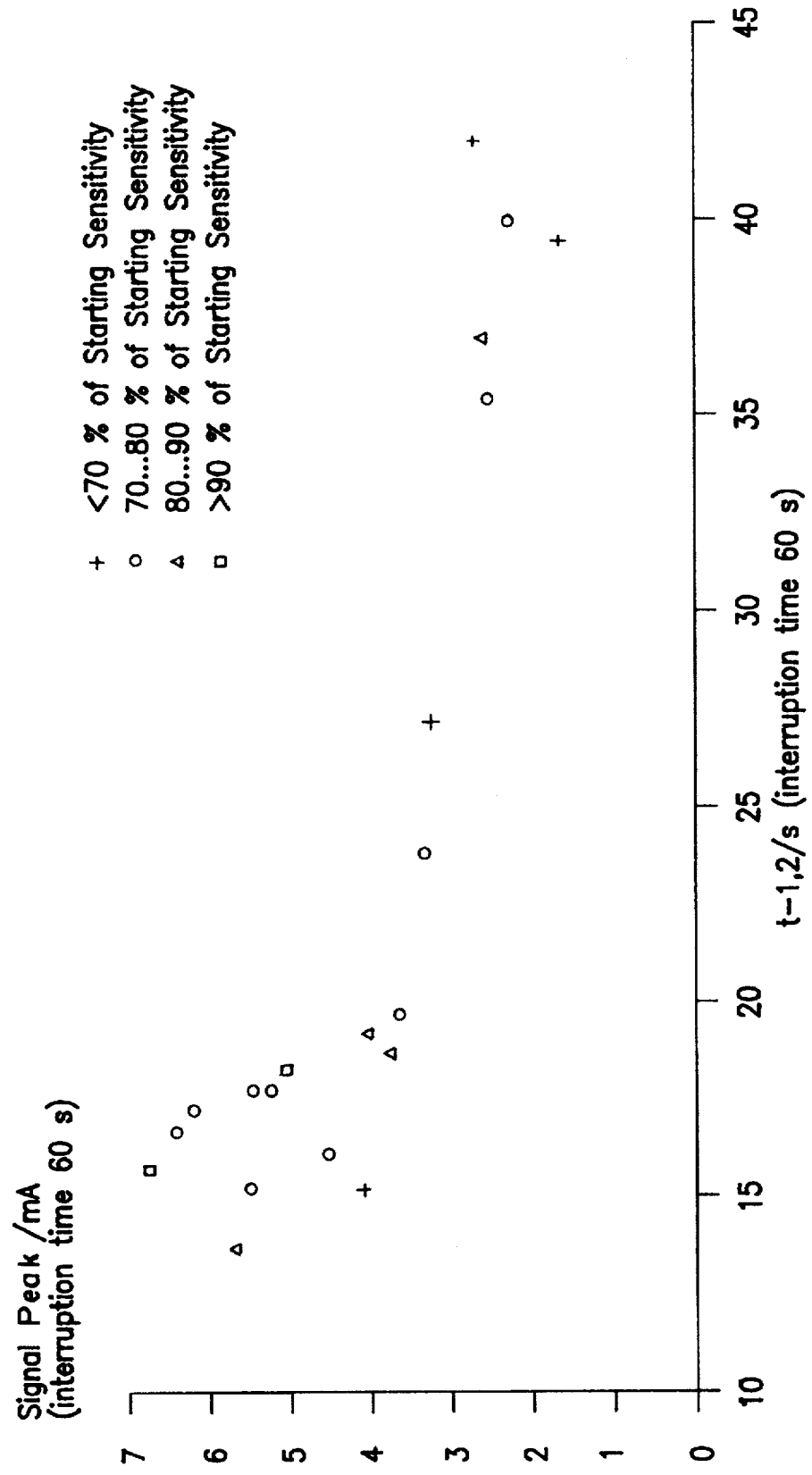
FIG. 2 shows the relationship between the signal peak value and the stabilization time for the tested sensors.

FIG. 2 shows the relationship between the signal peak value and the stabilization time for the tested sensors. The parameter used is the sensitivity loss over the past life. These results show that, depending on the state of consumption of the sensors, results which can be well differentiated can be attained, and a classification into sensors with little, intermediate and high aging is possible.

The object of these tests was to display the test state of an electrochemical gas sensor of a specific age—initially in particular the oxygen sensor—in the display of a gas analysis device.

For this purpose, numerous oxygen sensors which had been used in flue gas measuring devices were tested. In the process, a relatively simple electric diagnosis process was invented, which can be used to determine when or whether an oxygen sensor was replaced.

The sensor must not be removed to perform this diagnosis. Instead, a small circuit is used to make it possible that after a key is pressed, the external circuit initially connected to the sensor is briefly interrupted and then reconnected again. When circuits are closed, the sensor shows a typical "transient." When a large number of transients was evaluated, a reliable criterion was discovered which permits reliable statements regarding the state of consumption of the sensor, which is in contrast to the previously known, rather inaccurate parameters of sensitivity loss and manufacturing date. It is therefore no longer necessary that these previously used criteria be used as a base for assessment.

Further possible applications for the method according to the invention are commercial sensors in which a load resistor is integrated in the sensor, and in which a voltage instead of a current is measured as a sensor signal. Here the electric circuit cannot be interrupted. In this case, the electrochemical processes in the sensor can be suppressed by impressing a suitable voltage onto the sensor; this corresponds to the interruption of an external circuit.

The process can be used also for the frequently used three-electrode sensors for toxic gases (with a third reference electrode for stabilizing the potential of the counterelectrode). This presupposes that the sensor is exposed to the toxic gas to be detected in a constant and known concentration, and that the circuit is interrupted by using an appropriate device.

In this way, this invention can be used, for example, for diagnosing oxygen sensors in flue gas analyzers. By using the method of the invention, the oxygen sensors can be used significantly longer than was the case previously, or that the testing of sent—in sensors will show—unlike previously observed—that the oxygen sensors were no longer functioning at all. This can be safely prevented by using the method according to the invention, since the loss in function is displayed.

We claim:

1. A method for determining the life expectancy of an amperometrical, electrochemical gas sensor by use of a circuit external to the gas sensor, the gas sensor adapted to detect a gas and having at least a pair of electrodes, said method comprising of:

a) initially exposing the gas sensor to an environment with a known and constant concentration of the gas to be detected by the gas sensor and connecting the external circuit to the gas sensor to draw a sensor signal through the external circuit;

b) disconnecting the external circuit from the gas sensor for a given period of time while the gas sensor is exposed to the gas, said given period of time being sufficiently long so that the electrodes of the gas sensor are completely saturated by the molecules of the gas to be detected by the gas sensor;

c) after the given period, reconnecting the external circuit to the gas sensor; and d) after the reconnecting of step c), evaluating the sensor signal to determine the life expectancy of the gas sensor.

2. The method according to claim 1, wherein the sensor signal has a peak value, and said step d) evaluates the peak value of the sensor signal.

3. The method according to claim 1, wherein the sensor signal has a steepness in its drop, and said step d) evaluates the steepness in the drop of the sensor signal shortly after reconnection in step c).

4. The method according to 1, wherein the sensor signal has a period of time required to stabilize the sensor signal after reconnecting in step c), and said step d) evaluates the stabilizing period of time.

5. The method according to claim 1, wherein the sensor signal has a steepness of the drop of the sensor signal shortly after reconnection in step c), a time required to stabilize the sensor signal after reconnection in step c), and a peak value of the sensor signal after reconnection in step c), and step d) evaluates the steepness of the signal's drop, the stabilization time and the peak value.

6. The method according to claim 1, wherein the gas sensor is an oxygen sensor with an internal load resistor.

7. The method according to claim 1, wherein the gas sensor is an oxygen sensor without an internal load resistor.

8. The method according to claim 1, wherein the gas is dissolved oxygen and the gas sensor is adapted to sense dissolved oxygen.

9. The method according to claim 1, wherein the gas sensor is a toxic gas sensor.

* * * * *